United States Patent
Haas (10) Patent No.: US 9,687,624 B2
(45) Date of Patent: Jun. 27, 2017

(54) PRESSURE SUPPORT SYSTEM WITH MASK FIT FEEDBACK DISPLAY

(75) Inventor: Michael W. Haas, Trafford, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 765 days.

(21) Appl. No.: 13/512,971

(22) PCT Filed: Nov. 16, 2010

(86) PCT No.: PCT/IB2010/055202
§ 371 (c)(1),
(2), (4) Date: May 31, 2012

(87) PCT Pub. No.: WO2011/073814
PCT Pub. Date: Jun. 23, 2011

(65) Prior Publication Data
US 2012/0240933 A1 Sep. 27, 2012

Related U.S. Application Data

(60) Provisional application No. 61/288,270, filed on Dec. 19, 2009.

(51) Int. Cl.
*A61M 16/06* (2006.01)
*A61M 16/00* (2006.01)

(52) U.S. Cl.
CPC ......... *A61M 16/06* (2013.01); *A61M 16/0051* (2013.01); *A61M 16/0605* (2014.02);
(Continued)

(58) Field of Classification Search
CPC .. A61M 2205/15; A61M 16/00–16/22; A61M 16/0633; A61M 16/0683; A61M 2230/04; A61M 2230/08; A61M 2230/10; A61M 2230/205; A61M 2230/30; A61M 2230/50; A61M 2230/60; A61M 2230/62;
(Continued)

(56) References Cited

U.S. PATENT DOCUMENTS

2003/0062040 A1 4/2003 Laurie
2004/0163648 A1* 8/2004 Burton ............... 128/204.21
(Continued)

FOREIGN PATENT DOCUMENTS

CN 1919376 A 2/2007
GB 2339392 A 1/2000
(Continued)

*Primary Examiner* — Lynne Anderson
*Assistant Examiner* — Elliot S Ruddie
(74) *Attorney, Agent, or Firm* — Michael W. Haas (57) ABSTRACT

A pressure support system configured to deliver a pressurized flow of breathable gas to the airway of a subject is further configured to provide information to a user position, fit or seal between the subject and the patient interface through which the pressurized flow of breathable gas is delivered. Such information may include, for example, a location on the patient interface at which the integrity of the seal is compromised, adjustments that could be made by the subject to enhance the interface between the patient interface and the subject, different types and/or sizes of patient interfaces that could be used to enhance the fit and seal between the system and the subject, and/or other information.

18 Claims, 3 Drawing Sheets

(52) U.S. Cl.
CPC . *A61M 2205/15* (2013.01); *A61M 2205/3344* (2013.01); *A61M 2205/3368* (2013.01); *A61M 2205/3375* (2013.01); *A61M 2205/3584* (2013.01); *A61M 2205/3592* (2013.01); *A61M 2205/502* (2013.01); *A61M 2205/52* (2013.01); *A61M 2205/581* (2013.01); *A61M 2205/583* (2013.01); *A61M 2205/6018* (2013.01); *A61M 2205/702* (2013.01)

(58) Field of Classification Search
CPC .... A61M 2230/63; A61B 5/00–5/0033; A61B 5/04085; A61B 5/05492; A61B 5/0878; A61B 5/6803; A61B 5/0476
USPC ............ 128/200.24, 202.22, 204.18, 204.21, 128/204.22, 204.23, 204.29, 206.21
See application file for complete search history.

(56) References Cited

U.S. PATENT DOCUMENTS

| | | | | |
|---|---|---|---|---|
| 2006/0237013 | A1* | 10/2006 | Kwok | A61M 16/06 128/204.23 |
| 2006/0254588 | A1* | 11/2006 | Brewer et al. | 128/204.18 |
| 2007/0089747 | A1* | 4/2007 | Liland et al. | 128/206.21 |
| 2010/0288279 | A1* | 11/2010 | Seiver et al. | 128/204.21 |
| 2011/0220107 | A1* | 9/2011 | Kimm et al. | 128/204.21 |

FOREIGN PATENT DOCUMENTS

| | | |
|---|---|---|
| WO | WO9930760 A1 | 6/1999 |
| WO | WO2006133494 A1 | 12/2006 |
| WO | WO2008028014 A2 | 3/2008 |

\* cited by examiner

PRESSURE SUPPORT SYSTEM WITH MASK FIT FEEDBACK DISPLAY

CROSS-REFERENCE TO RELATED APPLICATIONS

This patent application claims the priority benefit under 35 U.S.C. §371 of international patent application no. PCT/IB2010/055202, filed Nov. 16, 2010, which claims the priority benefit under 35 U.S.C. §119(e) of U.S. Provisional Application No. 61/288,270 filed on Dec. 19, 2009, the contents of which are herein incorporated by reference.

BACKGROUND OF THE INVENTION

1. Field of the Disclosure

The invention relates to a pressure support system and method that provides an indication to a user of the fit and/or position of a patient interface configured to deliver a pressurized flow of breathable gas to the airway of a subject.

2. Description of the Related Art

Pressure support systems configured to deliver a pressurized flow of breathable gas to the airway of a subject are known. Generally, these systems include a patient interface configured to engage that airway of the subject to deliver the pressurized flow of breathable gas from the pressure support system to the airway. Conventional patient interfaces are subject to discomfort and/or leakage that interferes with the provision of pressure support therapy. Discomfort or leakage is sometimes caused by misalignment with the face of the subject and/or misfit between the patient interface and the face of the subject.

SUMMARY OF THE INVENTION

Accordingly, it is an object of the present invention to provide a pressure support system that overcomes the shortcomings of conventional pressure support system. This object is achieved according to one embodiment of the present invention by providing a pressure support system that includes a housing and a pressure generator disposed in the housing. The pressure generator is configured to generate a flow of gas for delivery to the airway of a subject. A patient circuit is coupled to the pressure generator to carry the flow of gas to a patient interface, which is adapted to be coupled to the airway of a user. A sensor is coupled to the patient interface to provide information related to fit or position of the patient interface on a face of the subject. A user interface is carried by the housing and is used to communicate information to such a subject. A processor disposed in the housing is coupled to the sensor and the output device. The processor controls the user interface, based on the information from the sensor, to communicate to such a subject the information related to fit or position of the patient interface.

It is yet another object of the present invention to provide a method of providing a pressurized flow of breathable gas to the airway of a subject that does not suffer from the disadvantages associated with conventional method. This object is achieved by providing a method that includes (1) generating a flow of breathable gas for delivery to the airway of a subject through a patient circuit and a patient interface that engages the face of the subject, wherein the flow of breathable gas is generated by a pressure generator contained within a housing; (2) receiving an output signal generated by a sensor operatively coupled to the patient interface that conveys information related to fit or position of the patient interface on a face of such a subject; and (3) communicating, to a user, information related to fit or position of the patient interface on such face of such a subject conveyed by the output signal generated by the sensors, wherein the user information is communicated to the user via a user interface carried by the housing.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As employed herein, the term "patient interface" or "patient interface device" refers to any suitable mechanism for communicating a flow of gas with an airway of a user and expressly includes, but is not limited to, non-invasive patient interfaces such as masks (e.g., without limitation, masks including support elements such as forehead supports and cheek pads and full face masks), nasal masks and combination nasal/oral masks.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
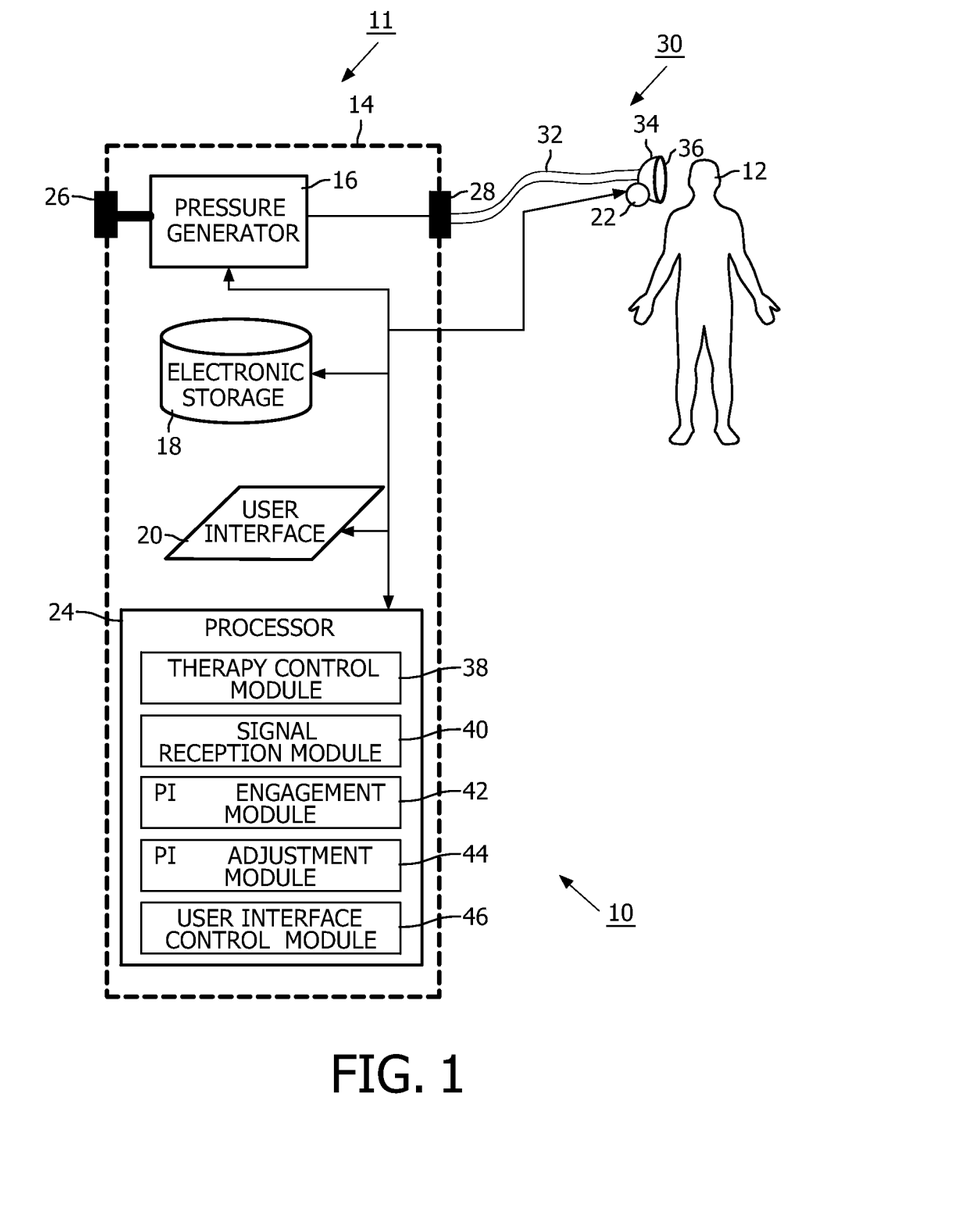
FIG. 1 schematically illustrates a pressure support system configured to deliver a pressurized flow of breathable gas to the airway of a subject, in accordance with one or more embodiments of the invention.

FIG. 1 illustrates a pressure support system 10 configured to deliver a pressurized flow of breathable gas to the airway of a subject 12. Pressure support system 10 includes a pressure generating system 11 that produces a flow of gas for delivery to an airway of subject 12. Pressure support system 10 further includes a patient circuit 30 that carries the flow of bas, and a patient interface 34 that communicates the flow of gas with an airway of subject 12, both of which are described below.

For purposes of the present invention, pressure generating system 11 is any device capable of generating a flow of breathing gas or providing gas at an elevated pressure. Examples of such pressure generating systems include a ventilator, CPAP device, or variable pressure device, e.g. an auto-titrating device, proportional assist ventilation (PAV®) device, proportional positive airway pressure (PPAP) device, C-Flex™ device, Bi-Flex® device, AFLEX, or a BiPAP® device manufactured and distributed by Philips Respironics of Murrysville, Pa., in which the pressure provided to the patient varies with the patient's respiratory cycle so that a higher pressure is delivered during inspiration than during expiration, or other pressure support device or medical ventilators.

Pressure generating system 11 includes a housing 14, a pressure generator 16, an electronic storage 18, a user interface 20, and a processor 24, and/or other components typically needed to perform the functions of a pressure support system and those of the present invention. Housing 14 is configured to provide a physical barrier between the inner workings of pressure generating system 11 and the environment. This barrier may protect the inner workings of the pressure generating system from contamination, breakage, and/or other physical disruptions. Housing 14 further defines an outer structure of the pressure generation device, and carries some of the components of the pressure support system 10 such that they are accessible to users (e.g., user interface 20 described below is disposed on an exposed surface of the housing). Generally, housing 14 defines a gas inlet 26 through which gas is received from one or more gas sources into system 10, and a gas outlet 28 through which the pressurized flow of breathable gas is dispensed from system 10.

Pressure generator 16 is disposed within housing 14, and is configured to generate the pressurized flow of breathable gas for delivery to the airway of subject 12. Pressure generator 16 may control one or more parameters of the pressurized flow of breathable gas (e.g., flow rate, pressure, volume, humidity, temperature, gas composition, etc.) for therapeutic purposes, or for other purposes. By way of non-limiting example, pressure generator 16 may be configured to control the flow rate and/or pressure of the pressurized flow of breathable gas to provide pressure support to the airway of subject 12. To generate the pressurized flow of breathable gas, pressure generator 16 may include one or more of a bellows, a blower, a turbine, a valve, and/or other devices configured to controllably pressurize gas.

In an exemplary embodiment of the present invention, pressure generator 16 is a mechanical pressure generator, such as a blower, bellows or piston, that receives ambient air, for example, at an inlet from the gas source. A pressure control valve (not shown) may be provided to control the pressure of the flow of breathing gas delivered to the patient via the patient circuit by restricting the flow to the patient, by diverting flow from patient circuit a combination thereof. The present invention further contemplates controlling the pressure of the flow of breathing gas delivered to the patient by controlling the operating speed of pressure generator 16, either alone or in combination with the valve noted above. Of course, the valve can be eliminated if operating speed alone is used to control the pressure of the flow of breathing gas delivered to the patient. Those skilled in the art can appreciate that other techniques for controlling the pressure of the flow of breathing gas delivered to the patient can be implemented in pressure generating system 11, either alone or in combination to those discussed above. For example, a flow restricting valve (not shown) can be provided upstream of pressure generator 16 that controls the flow of gas to pressure generator 16, and, hence, the pressure of the flow of gas output for delivery to the patient.

Typically, the source of breathing gas is the ambient atmosphere, where its pressure is subsequently elevated for delivery to the patient by the pressure generating system. It is to be understood, that other sources of breathing gas are contemplated by the present invention, such as oxygen or an oxygen mixture from an oxygen source. It is to be further understood, that the present invention contemplates that pressurized air can be provided to the airway of the patient directly from a tank of pressurized air via the patient circuit without using a pressure generator, such as a blower, bellows or piston, to increase the pressure of the air. Of course, a pressure regulator, such as a valve would be required to control the pressure of the gas delivered to the patient. The important feature with respect to the present invention is that pressurized breathing gas is provided in the patient circuit for delivery to the patient, not necessarily the source or manner in which the pressurized breathing gas is generated.

Although not shown in FIG. 1, the present invention also contemplates providing a secondary flow of gas, either alone or in combination with the primary flow of gas (arrow A) from atmosphere. For example, a flow of oxygen from any suitable source can be provided upstream to pressure generator 16 or downstream of the pressure generator in the patient circuit or at the patient interface device to control the fraction of inspired oxygen delivered to the patient.

The flow of breathable gas is delivered to the airway of subject 12 from a gas outlet 28 of housing 14 via a patient circuit 30. Patient circuit 30 is configured to communicate the flow of breathable gas generated by pressure generating system 11 to the airway of subject 12. To this end, patient circuit 30 is typically a flexible conduit 32 having a first end coupled to outlet 28, and a second end coupled to patient interface 34. It is to be understood that various components may be provided in or coupled to patient circuit 30. For example, a bacteria filter, pressure control valve, flow control valve, sensor, meter, pressure filter, humidifier and/or heater can be provided in or attached to the patient circuit. Likewise, other components, such as mufflers and filters can be provided at the inlet 26 of pressure generator 16 and at other locations along the gas flow path.

Patient interface device 34 is any device suitable for communicating an end of conduit 32 with the airway of the patient, more specifically, for communicating gas from the end of the conduit to the airway. Examples of suitable patient interface devices include a nasal mask, oral mask or mouthpiece, nasal/oral mask, nasal cannula, trachea tube, intubation tube, hood or full face mask. It is to be understood that this list of suitable interface devices is not intended to be exclusive or exhaustive. In one exemplary embodiment, patient interface 34 is a mask that encloses one or more external orifices of the airway of subject 12 (e.g., nares and/or mouth). To enclose one or more external orifices of the airway of subject 12, patient interface 34 forms a gas delivery opening 36. Around the rim of gas delivery opening 36, patient interface 34 engages the face of the subject 12 such that the pressurized flow of breathable gas is delivered to the one or more external orifices of the airway of subject 12 without substantial contamination from ambient atmosphere. A typical nasal mask includes a frame and a cushion supported on the frame. The cushion is the portion of the patient interface that contacts the surface of the user.

Although gas delivery circuit 30 is illustrated in FIG. 1 as a single-limbed circuit for the delivery of the pressurized flow of breathable gas to the airway of subject 12, this is not intended to be limiting. The scope of this disclosure includes double-limbed circuits having a first limb configured to both provide the pressurized flow of breathable gas to the airway of subject 12, and a second limb configured to selectively exhaust gas from gas delivery circuit 30 (e.g., to exhaust exhaled gases).

In one embodiment, electronic storage 18 comprises electronic storage media that electronically stores information. The electronic storage media of electronic storage 18 may include one or both of system storage that is provided integrally (i.e., substantially non-removable) with pressure support system 10 and/or removable storage that is removably connectable to system 10 via, for example, a port (e.g., a USB port, a firewire port, etc.) or a drive (e.g., a disk drive, etc.). Electronic storage 18 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 18 may store software algorithms, information determined by processor 24, information received via user interface 20, and/or other information that enables system 10 to function properly. Electronic storage 18 may be (in whole or in part) a separate component within system 10, or electronic storage 18 may be provided (in whole or in part) integrally with one or more other components of system 10 (e.g., generator 16, user interface 20, processor 24, etc.).

User interface 20 is carried by housing 14, and is configured to provide an interface between pressure support system 10 and a user through which the may provide information to and receive information from the system. This enables data, cues, results, and/or instructions and any other communicable items, collectively referred to as "information," to be communicated between the user and one or more of pressure generator 16, electronic storage 18, and/or processor 24. The user may include one or more of subject 12, a caregiver, a therapy decision-maker, a spouse or partner, and/or other users. Examples of interface devices suitable for inclusion in user interface 20 include a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 20 includes a plurality of separate interfaces.

It is to be understood that other communication techniques, either hard-wired or wireless, are also contemplated by the present invention as user interface 20. For example, the present invention contemplates that user interface 20 may be integrated with a removable storage interface provided by electronic storage 18. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 20 include, but are not limited to, an RS-232 port, RF link, an IR link, modem (telephone, DSL, cable or other), and/or a transmitter/receiver. In short, any technique for communicating information with system 10 is contemplated by the present invention as user interface 20.

The present invention also contemplates that interface 20 can be used to provide information to control the operation of the pressure generating system, such as on/off, alarms, pressure changes/settings, ramp settings, humidity settings, and/or any other inputs or settings used to operate a pressure support system. These system control settings can also be provided via one or more other user interfaces separate from user interface 20.

Pressure support system 10 includes a sensor 22 is configured to generate output signals conveying information related to the engagement between patient interface 34 and the face of subject 12. In an exemplary embodiment, sensor 22 monitors the portion of patient interface 34 around the edge of gas delivery opening 36, which is typically the cushion. In particular, sensor 22 generates an output signal that conveys information about the fit or engagement of patient interface 34 with the face of subject 12 while the patient interface 34 is installed on or being fitted to the face of subject 12. This information may include, for example, an indication of the security (or lack of security) of the interface between the face of the subject and the patient interface 34 at specific locations around the edge of gas delivery opening 36.

In one embodiment, sensor 22 includes pressure sensors disposed in or on the cushion of patient interface. The output signals generated by these pressure sensors indicate the pressure of the engagement between the cushion and the face of the subject around the edge of gas delivery opening 36.

In one embodiment, sensor 22 includes audio transducers disposed around the edge of gas delivery opening 36. During the delivery of the pressurized flow of breathable gas through patient interface 34, leakage of gas from within the patient interface to ambient atmosphere at the engagement between patient interface 34 and the face of the subject tends to generate sound. The sound transducers would capture this sound such that the output signals generated by the sound transducers could be analyzed to determine the location(s) at which gas was leaking from inside of patient interface 34 to atmosphere.

In yet another embodiment, sensor 22 includes temperature sensors disposed around the edge of gas delivery opening 36. Leakage of gas from inside patient interface 34 to atmosphere will tend to cause a reduction in temperature at the position of the leak (e.g., caused by the flow of fluid through the leak). As such, the output signals generated by the temperature sensors could be analyzed to determine the location(s) at which gas was leaking from inside patient interface 34 to atmosphere. Also, contact between the cushion and the user may be sensed by such temperature sensor.

It will be appreciated that these examples of the types of sensors that may be included in sensor 22 is not intended to be limiting. Any sensors that generate an output signal convey information related to the fit or position of patient interface 34 on the face of subject 12 while patient interface 34 is installed on subject 12 are included within the scope of this disclosure.

Although sensor 22 is schematically illustrated as a single sensor at a single location in pressure generator 16, this is for illustrative purposes only. The sensor 22 may include a plurality of sensors which may be located proximately or separately with respect to each other. Similarly, this disclosure is not limited to sensors located at the edge of gas delivery opening 36 on the cushion, or even within patient interface 34. To the extent that one or more sensors generate an output signal providing the functionality attributed herein to sensor 22, such sensors may be implemented in system 10 as discussed without regard for position or location within system 10. For example, sensor 22 may include one or more sensors disposed in pressure generator 16, within (or in communication with) conduit 32, and/or other locations.

Processor 24 is configured to provide information processing capabilities in pressure support system 10. As such, processor 24 may include one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some implementations, processor 24 may include a plurality of processing units. These processing units may be physically located within the same device (e.g., pressure generator 16), or processor 24 may represent processing functionality of a plurality of devices operating in coordination.

By way of non-limiting example, in one embodiment, processor 24 includes a first processor and a second processor. The first processor is located outside of housing 14 (e.g., carried by patient interface 34 and/or conduit 32) configured to receive the output signal of sensor 22, and to provide at least some of the information processing functionality attributed herein to processor 24 (e.g., preliminary processing of the output signal of sensor 22). The second processor is located inside of second section 44, and is configured to receive information from the first processor, and to provide other portions of the information processing functionality attributed herein to processor 24.

As is shown in FIG. 1, processor 24 is configured to execute one or more computer programs or modules. The one or more computer program modules may include one or more of a therapy control module 38, an signal reception module 40, a patient interface (PI) engagement module 42, a patient interface (PI) adjustment module 44, a user interface control module 46, and/or other modules. Processor 24 may be configured to execute modules 38, 40, 42, 44 and/or 46 by software, hardware, firmware, some combination of software, hardware, and/or firmware; and/or other mechanisms for configuring processing capabilities on processor 24.

It should be appreciated that although modules 38, 40, 42, 44, and 46 are illustrated in FIG. 1 as being co-located within a single processing unit, in implementations in which processor 24 includes multiple processing units, one or more of modules 38, 40, 42, 44 and/or 46 may be located remotely from the other modules. The description of the functionality provided by the different modules 38, 40, 42, 44 and/or 46 described below is for illustrative purposes, and is not intended to be limiting, as any of modules 38, 40, 42, 44 and/or 46 may provide more or less functionality than is described. For example, one or more of modules 38, 40, 42, 44 and/or 46 may be eliminated, and some or all of its functionality may be provided by other ones of modules 38, 40, 42, 44 and/or 46. As another example, processor 24 may be configured to execute one or more additional modules that may perform some or all of the functionality attributed below to one of modules 38, 40, 42, 44 and/or 46.

Therapy control module 38 is configured to control pressure generator 16 to generate the pressurized flow of breathable gas in accordance with the therapy regime. By way of non-limiting example, processor 24 may control pressure generator 16 such that pressure support provided to subject 12 via the pressurized flow of breathable gas includes, one or more of non-invasive ventilation, positive airway pressure support, bi-level support, BiPAP®, and/or other types of pressure support therapy.

Signal reception module 40 is configured to receive an output signal generated by sensor 22. Signal reception module 40 may receive an output signal that has been transmitted to processor 24 wirelessly or via a wired connection. As such, processor 24 may be communicatively coupled with sensor 22 to enable signal reception module 40 to receive the output signal. Of course, patient interface 34 and pressure generating system 11 may include the necessary hard, such as transmitters, receivers, transceivers, etc. for providing the hardwired or wireless communication.

Patient interface engagement module 42 is configured to determine information related to the engagement of patient interface 34 on the face of subject 12. Patient interface engagement module 42 determines this from the output signal received by signal reception module 40. In one embodiment, patient interface engagement module 42 determines the location or locations (e.g., on patient interface 34 and/or on subject 12) at which the engagement or contact between patient interface 34 and subject 12 are secure, and/or the location or locations at which the engagement between patient interface 34 and subject 12 are inadequate (e.g., will permit unacceptable leakage from inside patient interface 34 to atmosphere, or is applying too great a pressure against the user).

For example, if sensor 22 includes pressure sensors disposed around the edge of gas delivery opening 36, patient interface engagement module 42 identifies locations around the edge of gas delivery opening 36 at which the pressure between patient interface 34 and the face of subject 12 are not sufficient to substantially seal the interior of patient interface 34 against the user. In addition, patient interface engagement module 42 can identify locations around the edge of gas delivery opening 36 at which the contact pressure of the patient interface is too great, which may cause the patient discomfort or tissue damage. As another example, if sensor 22 includes temperature sensors disposed around the edge of gas delivery opening 36, patient interface engagement module 42 identifies locations around the edge of gas delivery opening 36 at which temperature indicates that gas is leaking to ambient atmosphere.

Patient interface adjustment module 44 is configured to determine adjustments that can be made to patient interface 34 to enhance the engagement between the patient interface and the face of subject 12. Such adjustments may include, for example, a direction in which patient interface 34 should be moved, an adjustment that should be made to a headgear holding patient interface 34 in place (e.g., to tighten or loosen a specific strap or set of straps, to tighten or loosen the headgear generally, and/or other adjustments), and/or other adjustments to patient interface 34. Other adjustments that may be determined by patient interface adjustment module 44 include suggestions of different types and/or sizes of patient interface 34 that would be a better fit with the shape of the face of subject 12. The patient interface adjustment module 44 determines the adjustments from the output signals received by signal reception module 40 and/or from the information related to the engagement of patient interface 34 with the face of subject 12 that is determined by patient interface engagement module 42.

User interface control module 46 is configured control user interface 20 to communicate to a user (e.g., subject 12, a care-provider, a therapy decision-maker, a spouse or partner, and/or other users) information related to fit or position of patient interface 34 on the face of subject 12 conveyed by the output signals received by signal reception module 40. This information may include information determined by patient interface engagement module 42 and/or patient interface adjustment module 44.

In this manner, pressure support system 10 of the present invention is configured to provide information to subject 12 related to the patient interface or interaction between subject 12 and pressure support system through which the pressurized flow of breathable gas is delivered. More specifically, such information is directed to the interaction between a subject 10 and a patient interface 36. Such information can pertain, for example, to the integrity and/or comfort of the patient interface so that adjustments can be made by the subject 12 to enhance the interface between system 10 and subject 12 and/or other information. Such adjustments can include moving or realigning patient interface 36 on the face, using a different type and/or size of patient interface, adjusting the tension of a headgear strap used to hold the patient interface on the user, or another other alteration that enhances the interface between system 10 and subject 12

Figure 2:
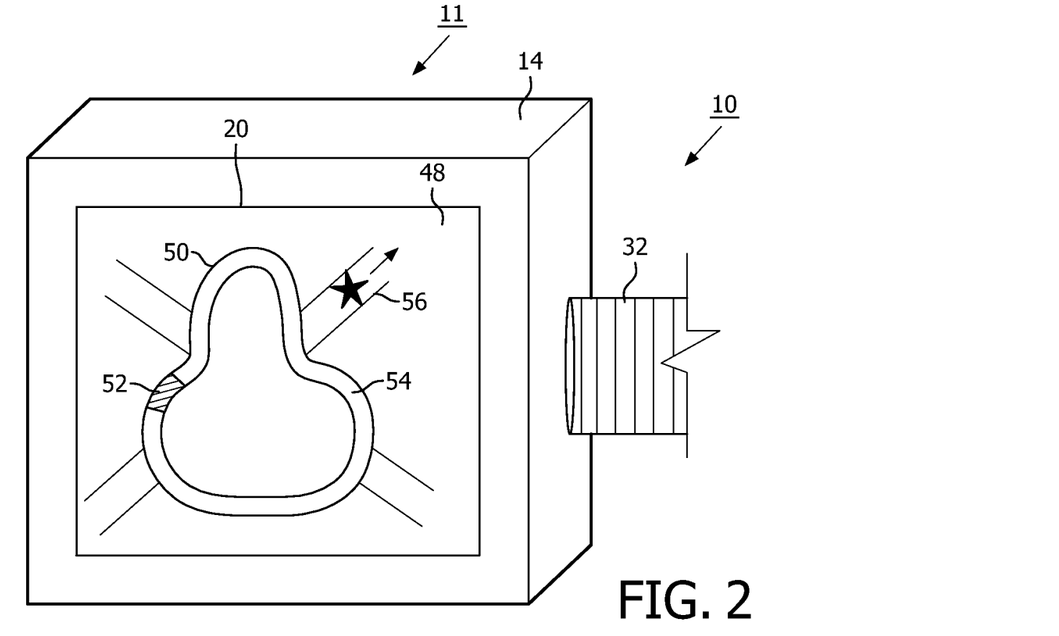
FIG. 2 illustrates a user interface of a pressure support system according to one or more embodiments of the invention.

In one embodiment, user interface 20 includes an electronic display screen carried by housing 14. FIG. 2 provides an illustration of how a user interface control module (similar to or the same as user interface control module 46 from FIG. 1) may control an electronic display screen 48 of user interface 20. In the implementation of electronic display screen 48 shown in FIG. 2, a view 50 (i.e., a representation) of a patient interface is shown. Different sections of view 50 may be manipulated on electronic display screen 48 to indicate to a user the status of the engagement of the patient interface at different locations on the patient interface and/or the face of the subject wearing the patient interface. It is be understood, that view 50 can depict any number of different types of patient interfaces and can assume any geometry or shape so as to provide such depiction, including depicting nasal cannula or portions thereof. In a broader aspect, the patient interface can include an invasive component, such as an endotracheal tube. In which case, view 50 can be used to show a portion of such a system so that the user (typically a caregiver) can use that view to position the endotracheal tube in the patient.

At a first location 52 on the patient interface, view 50 indicates that gas is leaking from within the patient interface to ambient atmosphere. This indication may include a color that indicates leakage (e.g., red, yellow, and/or other colors). The shade of the color (e.g., brightness, pureness, and/or other aspects of shade or hue) may indicate the amount of leakage present at first location 52. The indication may include flashing at first location 52. The rate, brightness, pulse length, and/or other aspects of the flashing may indicate the amount of leakage present at first location 52. The indication may include an icon representing leakage (e.g., an arrow pointing out of the patient interface at first location 52). The size, shape, color, brightness, and/or other aspects of the icon may indicate the amount of leakage present at first location 52.

In one embodiment, at a second location 54 on the patient interface, view 50 indicates that the engagement between the patient interface and the face of the subject is secure. This indication may include a color that indicates a secure engagement (e.g., green, grey, and/or other colors). Of course, there can be multiple locations on the patient interface where the seal is not secure. In which case, more than one location on view 50 can provide an indication that the patient interface is not properly located or seated on the user.

In one embodiment, electronic display screen 48 provides a suggested adjustment of the patient interface to the user. For example, the suggested adjustment may indicate a direction in which the patient interface should be shifted on the face of the subject. This direction may be indicated by an icon (e.g., an arrow). The size, shape, color, brightness, and/or other aspects of the icon may indicate the distance that the subject interface should be shifted. The direction may be indicated by an animation that shows the patient interface or a portion thereof in view 50 being shifted in the appropriate direction. The amount by which the patient interface is shifted in view 50 may indicate the distance that the patient interface should be shifted on the face of the subject. The direction by which the patient interface should be shifted may be conveyed to the user by text displayed on electronic display screen 48. Other mechanisms for indicating on electronic display screen 48 how the patient interface should be shifted on the face of the subject may be used.

As one example of a suggested adjustment to the patient interface, electronic display screen 48 may indicate an adjustment to a headgear that is holding the patient interface in place on the head of the subject. This adjustment may include a general tightening, loosening, or shifting of the headgear, and/or one or more specific adjustments to the headgear. A specific adjustment to the headgear may include the tightening, loosening, and/or shifting of one or more specified straps. In view 50, specific adjustments to the headgear include an indication that a first strap 56 should be adjusted. The indication that first strap 56 should be adjusted may be conveyed by coloring first strap 56 in view 50. The amount of adjustment may be conveyed by the shade or hue of the color, the brightness of the color, and/or other aspects of the color. The indication that first strap 56 should be adjusted may be conveyed to the user by an icon (e.g., an arrow) identifying first strap 56. The size, shape, color, brightness, and/or other aspects of the icon may indicate the amount by which first strap 56 should be adjusted. The indication that first strap 56 should be adjusted may be made by an animation showing the appropriate action that should be taken with respect to first strap 56. The amount by which first strap 56 is to be adjusted (e.g., tightened, loosened, shifted, and/or otherwise adjusted) may be conveyed by the amount that first strap 56 is adjusted in the animation. The indication that first strap 56 should be adjusted may be provided to the user in the form of text describing the adjustment that should be made to the headgear. Other mechanisms for indicating on electronic display screen 48 how the headgear holding the patient interface in place should be adjusted may be used.

As one example of a suggested adjustment to the patient interface, electronic display screen 48 may indicate an adjustment to component of the patient interface, such as a change of position of a forehead support, inflation/deflation of the cushion or portions of the cushion, or any other adjustment that is permitted by the patient interface. The amount of adjustment may be conveyed by the shade or hue of the color, the brightness of the color, and/or other aspects of the color. The indication that a particular component should be adjusted may be conveyed to the user by an icon (e.g., an arrow). The size, shape, color, brightness, and/or other aspects of the icon may indicate the amount by which the component should be adjusted. The indication that patient interface component should be adjusted may be made by an animation showing the appropriate action that should be taken with respect to that component, such as an animation showing the forehead support being moved up, down, inward, outward, etc., relative the shell or the patient. The amount by which the component of the patient interface is to be adjusted may be conveyed by the animation. The indication that the component of the patient interface should be adjusted may also be provided to the user in the form of text describing the adjustment that should be made to the component of the patient interface. Other mechanisms for indicating on electronic display screen 48 how the component of the patient interface can be adjusted may be used.

As one example of the adjustment that should be made to the patient interface, electronic display screen 48 may indicate that a different patient interface or component thereof should be used. This indication may be provided to the user by showing the type of the appropriate patient interface, if the current patient interface is of the wrong type. This indication may be provided by the user by showing the type of component, such as cushion, mask shell, or headgear, that may be appropriate if the current components of the patient interface are not provided the proper fit. The indication that a different patient interface should be used may be provided to the user by showing a patient interface that is bigger or smaller than the representation of the patient interface shown in view 50, if the current patient interface is the wrong size. The indication that a different patient interface should be used may be provided to the user by displaying an identification (e.g., make/model name, model number, and/or other identifier) that identifies the appropriate patient interface. Other mechanisms for indicating on electronic display screen 48 that a different patient interface should be installed on the face of the subject may be used.

Figure 3:
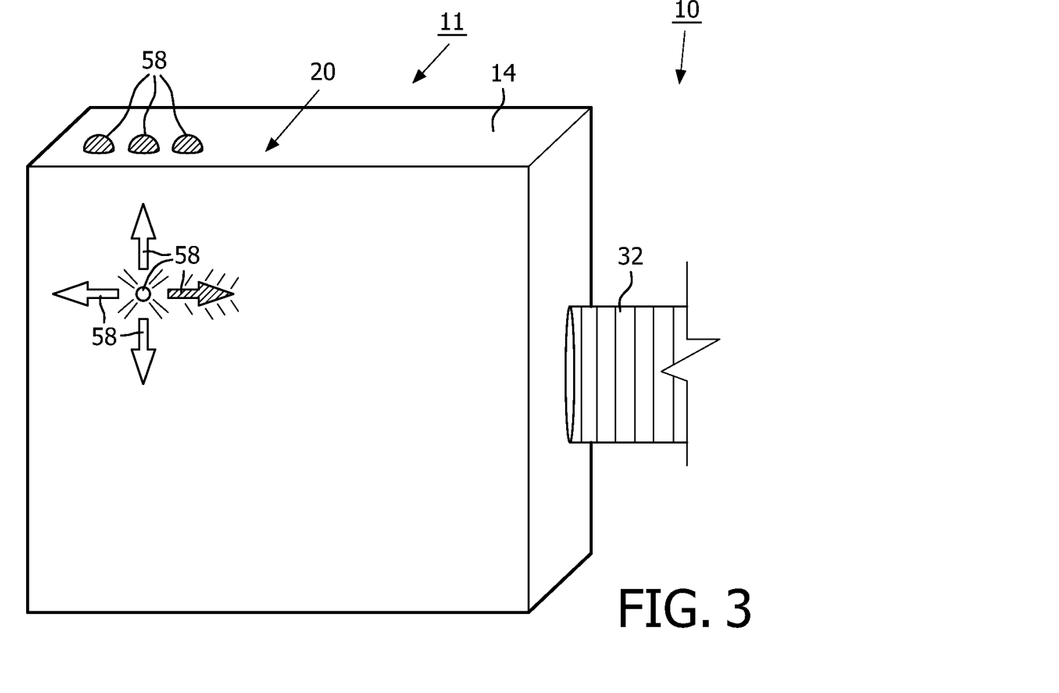
FIG. 3 illustrates a user interface of a pressure support system according to one or more embodiments of the invention.

In one embodiment, user interface 20 includes one or more indicator lights carried by housing 14. FIG. 3 provides an illustration of how a user interface control module (similar to or the same as user interface control module 46 from FIG. 1) may control indicator lights 58 of user interface 20. In the implementation of user interface 20 shown in FIG. 3, a plurality of indicator lights 58 are included. One or more of indicator lights 58 may be manipulated to indicate to a user the status of the engagement of the patient interface at different locations on the patient interface and/or the face of the subject wearing the patient interface.

In one embodiment, individual ones of indicator lights 58 represent individual locations on the patient interface. Although not shown in FIG. 3, indicator lights 58 may even be arranged in the shape patient contacting portion the patient interface for more intuitive interpretation by the user. If gas is leaking from within the patient interface to ambient atmosphere at a first location on the patient interface, the corresponding one of indicator lights 58 may be manipulated. This manipulation may include causing indicator lights 58 to shine with a color that indicates leakage (e.g., red, yellow, and/or other colors). The shade of the color (e.g., brightness, pureness, and/or other aspects of shade or hue) may indicate the amount of leakage present at the first location. The manipulation may include flashing the appropriate one of indicator lights 58. The rate, brightness, pulse length, and/or other aspects of the flashing may indicate the amount of leakage present. The manipulation may include the illumination of the appropriate one of indicator lights 58. The brightness, color, and/or other aspects of the illumination given off by the appropriate one of indicator lights 58 may indicate the amount of leakage present.

Where individual ones of indicator lights 58 do not correspond to specific locations on the patient interface, the manipulation of indicator lights 58 may first indicate a specific location, and then indicate the adjustment that should be made at that adjustment. For example, each of the positions on the patient interface may be numbered, and one or more of indicator lights 58 may flash a number of times indicating which position is leaking.

In one embodiment, indicator lights 58 provide a suggested adjustment of the patient interface to the user. For example, the suggested adjustment may indicate a direction in which the patient interface should be shifted on the face of the subject. This direction may be indicated by a shape of an indicator light 58 that is manipulated (e.g., an arrow). The size, shape, color, brightness, and/or other aspects of the shaped one of indicator lights 58 that is manipulated may indicate the distance that the patient interface should be shifted. Other mechanisms for indicating with indicator lights 58 how the patient interface should be shifted on the face of the subject may be used.

As one example of a suggested adjustment to the patient interface, indicator lights 58 may indicate an adjustment to a headgear that is holding the patient interface in place on the head of the subject. This adjustment may include a general tightening, loosening headgear, or shifting of the headgear, and/or one or more specific adjustments to the headgear. A specific adjustment to the headgear may include the tightening, loosening, and/or shifting of one or more specified straps. In one embodiment, indicator lights 58 include a first set of indicator lights that correspond to the patient interface and a second set of indicator lights that correspond to the headgear holding the patient interface. By manipulating the second set of indicator lights separately from the first set of indicator lights, user interface 20 may convey to the user how the headgear should be adjusted. In using indicator lights 58 to indicate how the headgear should be adjusted, the color, periodic pattern (e.g., flashing), brightness, and/or other aspects of the illumination of indicator lights 58 may be manipulated.

As another example of a suggested adjustment to the patient interface, indicator lights 58 may indicate an adjustment to component of the patient interface, such as a change of position of a forehead support, inflation/deflation of the cushion or portions of the cushion, or any other adjustment that is permitted by the patient interface. The amount of adjustment may be conveyed by the color, periodic pattern, brightness, combination of lights illuminated, and/or other aspects of indicator lights 58.

As one example of the adjustment that should be made to the patient interface, indicator lights 58 may indicate that a different patient interface should be used. This indication may be provided to the user by illuminating or flashing a specific one or more of indicator lights 58 that are designated to correspond to changing the patient interface. The color, periodic pattern, brightness, combination of lights illuminated, and/or other aspects of indicator lights 58 may be manipulated to indicate if a different size and/or type of patient interface should be used. Other mechanisms for indicating on indicator lights 58 that a different patient interface should be installed on the face of the subject may be used.

Figure 4:
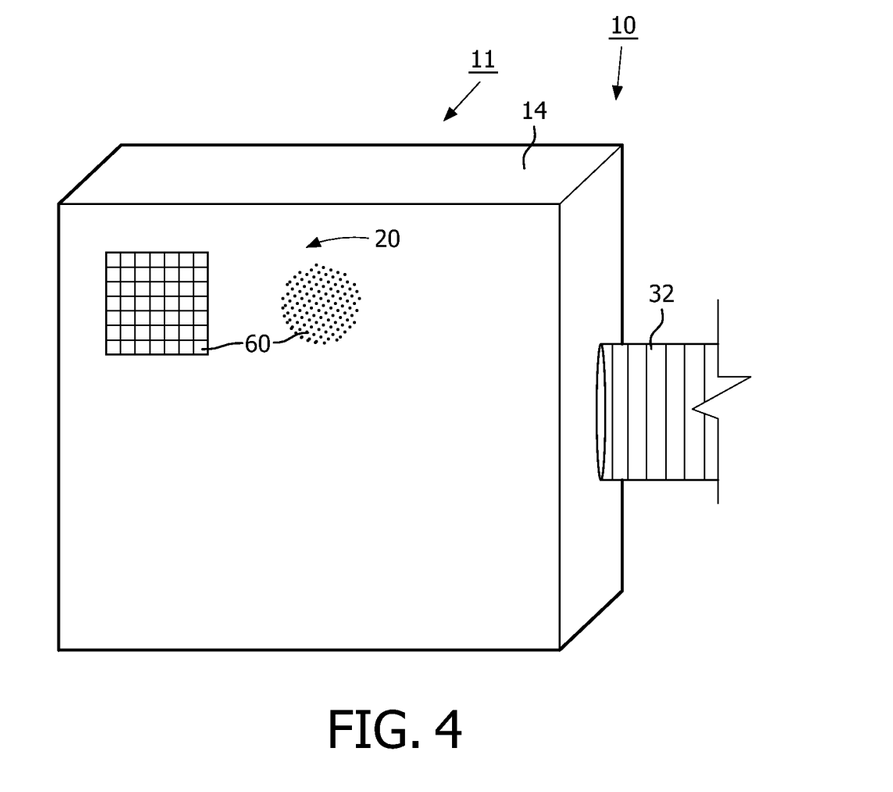
FIG. 4 illustrates a user interface of a pressure support system according to one or more embodiments of the invention.

In one embodiment, user interface 20 includes one or more audio speakers carried by housing 14. FIG. 4 provides an illustration of how a user interface control module (similar to or the same as user interface control module 46 from FIG. 1) may control one or more audio speakers 60 of user interface 20. The audio speakers 60 are driven to indicate to a user the status of the engagement of the patient interface at different locations on the patient interface and/or the face of the subject wearing the patient interface, and/or adjustments that could or should be made to the patient interface that would enhance the engagement between the patient interface and the face of the subject. Driving the audio speakers 60 to provide such indications may include driving audio speakers 60 to generate audio stating engagement status (e.g., at specific locations), adjustments that should be made to the position of the patient interface, adjustments that should be made to a headgear holding the patient interface in place on the head of the subject, alternate patient interface that should be used, and/or other indications of fit and/or position of the patient interface on the face of the subject. However, this should not be viewed as limiting. It will be appreciated that rather than expressly stating the status information and/or adjustments to be made, audio speakers 60 may be driven to generate alarms that correspond to the indicated status and/or adjustment(s). Other mechanisms for indicating information related to the fits and/or position of the patient interface using audio speakers 60 are contemplated.

Returning back to FIG. 1, as was described above, in one embodiment user interface 20 includes removable electronic storage media and/or a communications link with some other electronic platform (e.g., via network, via direct connection, wireless link, hard wired link, and/or other communications link). This enables user interface 20 carried by housing 14 to convey information to a user that is located remotely from the therapeutic setting in which system 10 is implemented. For example, information related to the fit and/or position of patient interface 34 on the face of subject 12 may be communicated with a caregiver and/or therapy decision-maker (e.g., a doctor, a researcher, etc.) that is responsible for the therapy of a plurality of subjects. Based on the information conveyed to such a user by user interface 20, the user may visit subject 12 to instruct them on how patient interface 34 should be adjusted to enhance the engagement between patient interface 34 and the face of subject 12.

The embodiments for communicating information related to the fit or position of patient interface 34 on the face of subject 12 to users discussed above have been described with respect to real-time feedback to the users. It will be appreciated that this is not intended to be limiting. In one embodiment, information about the fit or position of patient interface 34 is stored to electronic storage 18, and then communicated to a user subsequent to treatment. The stored information may include the output signal generated by sensor 22, information determined by patient interface engagement module 42, information determined by patient interface adjustment module 44, and/or other information related to the fit or position of patient interface 34 on the face of subject 12. This embodiment would, for example, enable a caregiver and/or therapy decision-maker to review the fit or position of patient interface 34 on the face of subject 12 during previous therapy. Based on this review, the caregiver and/or therapy decision-maker could provide recommendations and/or instruction to subject 12 on how to enhance the engagement between patient interface 34 and the face of subject 12 during subsequent therapy. The recommendations and/or instruction could include, for instance, a different patient interface 34, instructions on how to adjust the headgear properly on the head of subject 12, instructions on correct positioning for patient interface 34 on the face of subject 12, and/or other recommendations or instructions.

The illustration of a display screen, indicator lights, and audio speakers separately in FIGS. 2-4, and the separate discussion of user interface 20 communicating information to a user remote from the therapeutic setting is not intended to be limiting. In one embodiment, user interface 20 includes some combination of display screen, indicator lights, audio speakers, and/or communication to a remote user, and some or all of these mechanisms for communicating information to users are used together to provide indications of the fit and/or position of the patient interface. For example, the types of indication for engagement status and/or adjustments described individually with respect to electronic display screen 48, indicator lights 58, and/or audio speakers 60 (shown in FIGS. 2, 3, and 4, respectively) may be used in combination with each other. Similarly, in one embodiment, user interface 20 provides real-time feedback about the fit or position of patient interface 34 on the face of subject 12 to one or more users, and system 10 stores information related to the fit or position of patient interface 34 on the face of subject 12 so that stored information from previous therapy sessions can be conveyed to one or more users via user interface 20.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pressure support system comprising:
(a) a housing;
(b) a pressure generator disposed in the housing, wherein the pressure generator is configured to generate a flow of gas for delivery to the airway of a subject;
(c) a patient circuit having a first end operatively coupled to the pressure generator to carry the flow of gas;
(d) a patient interface coupled to a second end of the patient circuit, wherein the patient interface is adapted to be coupled to an airway of the subject, the patient interface having a seal surface where the patient interface is configured to create a seal with a face of the subject, the seal formed by sealing engagement between the patient interface and the face of the subject;
(e) a sensor operatively coupled to the patient interface, wherein the sensor is adapted to provide information related to fit or position of the patient interface on the face of the subject at a plurality of individual physical location along the seal surface;

(f) a user interface carried by the housing, wherein the user interface is configured to communicate information to the subject;

(g) a processor disposed in the housing and operatively coupled to the sensor, wherein the processor controls the user interface, based on the information from the sensor, to communicate to the subject the information related to fit or position of the patient interface, and wherein the information related to fit or position of the patient interface comprises:

(i) an identification of one or more of the individual physical locations where the sealing engagement between the patient interface and the face of the subject is inadequate, and (ii) a suggested adjustment which, if made, would enhance the engagement between the patient interface and the face of the subject to improve the seal on the face of the subject;

wherein the user interface is adapted to provide a visual representation of at least a portion of a geometry of the patient interface, and wherein the processor controls the user interface to indicate, by highlighting one or more portions of the visual representation that correspond to the one or more individual physical locations along the seal surface where the sealing engagement is inadequate, the information related to fit or position of the patient interface.

2. The system of claim 1, wherein the user interface comprises an electronic display and one or more of an indicator light, an audio speaker, removable electronic storage, or an electronic transmitter.

3. The system of claim 1, further comprising a storage system operatively coupled to the processor, wherein the storage system stores a record of the information related to fit or position of the patient interface.

4. The system of claim 1, further comprising a communication link adapted to communicate the information related to fit or position of the patient interface to a remote location.

5. A method of providing feedback to a subject regarding a fit of a patient interface, the method comprising:

generating a flow of breathable gas for delivery to an airway of a subject through a patient circuit and a patient interface that engages a face of the subject, wherein the flow of breathable gas is generated by a pressure generator contained within a housing;

sealing the patient interface on the face of the subject with a seal formed by sealing engagement between the patient interface and the face of the subject;

receiving an output signal generated by a sensor operatively coupled to the patient interface that conveys information related to fit or position of the patient interface on the face of the subject at a plurality of individual physical locations along the seal;

communicating the information related to fit or position of the patient interface on the face of the subject conveyed by the output signal generated by the sensor via a user interface carried by the housing, wherein the information related to fit or position of the patient interface comprises:

(a) an identification of one or more of the individual physical locations where the sealing engagement between the patient interface and the face of the subject is inadequate, and (b) a suggested adjustment which, if made, would enhance the engagement between the patient interface and the face of the subject to improve the sealing engagement with the face of the subject; and providing, via the user interface a visual representation of at least a portion of a geometry of the patient interface, and controlling the visual representation to indicate, by highlighting one or more portions of the visual representation that correspond to the one or more individual physical locations along the seal surface where the sealing engagement is inadequate, the information related to fit or position of the patient interface.

6. The method of claim 5, wherein the user interface comprises an electronic display and one or more of an indicator light, an audio speaker, removable electronic storage, or an electronic transmitter.

7. The method of claim 5, further comprising storing a record of the information related to fit or position of the patient interface on a storage system.

8. The method of claim 5, further comprising communicating the information related to fit or position of the patient interface to a remote location.

9. A system configured to provide a pressurized flow of breathable gas to an airway of a subject, the system comprising:

means for generating the pressurized flow of breathable gas for delivery to the airway of the subject through a patient circuit and a patient interface that engages a face of the subject, wherein the pressurized flow of breathable gas is generated by a pressure generator contained within a housing;

means for sealing the patient interface on the face of the subject, the means for sealing formed by sealing engagement between the patient interface and the face of the subject;

means for receiving an output signal generated by a sensor operatively coupled to the patient interface that conveys information related to fit or position of the patient interface on the face of the subject at a plurality of individual physical locations along the means for sealing; and means for communicating information related to fit or position of the patient interface on the face of the subject conveyed by the output signal generated by the sensor via a user interface carried by the housing, wherein the means for communicating is configured to communicate:

(a) an identification of one or more of the individual physical locations along the means for sealing where the sealing engagement between the patient interface and the face of the subject is inadequate, and (b) a suggested adjustment which, if made, would enhance the engagement between the patient interface and the face of the subject to improve the sealing engagement with the face of the subject; and means for providing a visual representation of at least a portion of a geometry of the patient interface and controlling the visual representation to indicate, by highlighting one or more portions of the visual representation that correspond to the one or more individual physical locations along the means for sealing where the sealing engagement is inadequate, the information related to fit or position of the patient interface.

10. The system of claim 9, wherein the means for communicating comprises one or more of an electronic display, an indicator light, an audio speaker, removable electronic storage, or an electronic transmitter.

11. The system of claim 9, further comprising means for storing a record of the information related to fit or position of the patient interface on a storage system.

12. The system of claim 9, further comprising means for communicating the information related to fit or position of the patient interface to a remote location.

13. The system of claim 1, wherein highlighting one or more portions of the visual representation comprises coloring the one or more portions of the visual representation, and wherein a shade of the coloring indicates an amount of leakage at a given physical location.

14. The method of claim 5, wherein highlighting one or more portions of the visual representation comprises coloring the one or more portions of the visual representation, and wherein a shade of the coloring indicates an amount of leakage at a given physical location.

15. The system of claim 9, wherein highlighting one or more portions of the visual representation comprises coloring the one or more portions of the visual representation, and wherein a shade of the coloring indicates an amount of leakage at a given physical location.

16. The system of claim 1, wherein the information related to the fit or position of the patient interface further comprises an identification of one or more of the individual physical locations where a pressure between the patient interface and the face of the subject causes discomfort or tissue damage in the subject.

17. The method of claim 5, wherein the information related to the fit or position of the patient interface further comprises an identification of one or more of the individual physical locations where a pressure between the patient interface and the face of the subject causes discomfort or tissue damage in the subject.

18. The system of claim 9, wherein the information related to the fit or position of the patient interface further comprises an identification of one or more of the individual physical locations where a pressure between the patient interface and the face of the subject causes discomfort or tissue damage in the subject.

* * * * *